United States Patent
Martinell Gisper-Sauch et al.

(10) Patent No.: US 6,503,226 B1
(45) Date of Patent: Jan. 7, 2003

(54) APPARATUS FOR ANGIOGRAPHY BY THE INJECTION OF $CO_2$

(75) Inventors: Enrique Martinell Gisper-Sauch, Barcelona (ES); Roger Ferrer Royo, Sant Cugat (ES); Jorge Mª Manzano Riera, Barcelona (ES)

(73) Assignee: Grupo Grifols, S.A., Parets del Valles (ES)

( * ) Notice: Subject to any disclaimer, the term of this patent is extended or adjusted under 35 U.S.C. 154(b) by 181 days.

(21) Appl. No.: 09/618,712

(22) Filed: Jul. 18, 2000

(30) Foreign Application Priority Data

Aug. 4, 1999 (ES) .............................................. 9901773

(51) Int. Cl.⁷ ................................................ A61H 1/00
(52) U.S. Cl. .................................. 604/151; 128/662.02
(58) Field of Search ................................ 604/151, 131, 604/154, 152, 155, 41, 247, 223; 128/662.02

(56) References Cited

U.S. PATENT DOCUMENTS

| | | | | |
|---|---|---|---|---|
| 5,249,579 A | * | 10/1993 | Hobbs et al. ........... | 128/662.02 |
| 5,807,334 A | * | 9/1998 | Hodosh et al. ............. | 604/131 |
| 5,814,020 A | * | 9/1998 | Gross ........................... | 604/41 |
| 5,913,844 A | * | 6/1999 | Ziemba et al. .............. | 604/154 |
| 5,925,022 A | | 7/1999 | Battiato et al. ............. | 604/208 |
| 5,928,197 A | * | 7/1999 | Niehoff ....................... | 604/155 |
| 5,947,929 A | * | 9/1999 | Trull ........................... | 604/152 |
| 6,030,368 A | * | 2/2000 | Anwar et al. ................ | 604/223 |
| 6,048,334 A | * | 4/2000 | Hirscman et al. ........... | 604/154 |
| 6,221,045 B1 | * | 4/2001 | Duchon et al. ............. | 604/151 |
| 6,241,708 B1 | * | 6/2001 | Reilly et al. ................. | 604/131 |
| 6,254,572 B1 | * | 7/2001 | Knipfer et al. ............. | 604/151 |
| 6,306,117 B1 | * | 10/2001 | Uber, III ..................... | 604/151 |
| 6,315,762 B1 | * | 11/2001 | Recinella et al. ............ | 604/247 |

FOREIGN PATENT DOCUMENTS

| EP | 0 446 715 A2 | 9/1991 |
|---|---|---|
| ES | 2 116 271 | 7/1998 |
| WO | 94 13204 A | 6/1994 |

* cited by examiner

Primary Examiner—Teresa Walberg
Assistant Examiner—Leonid Fastovsky
(74) Attorney, Agent, or Firm—Darby & Darby

(57) ABSTRACT

The apparatus comprises a transportable unit with a support base which is provided with wheels and which carries a source for the supply of $CO_2$ under regulated pressure, having a support foot provided, at the top, with an articulated arm carrying a programming and control screen and means for receiving an exchangeable metering device capable of receiving the $CO_2$ by way of ducts coming from the $CO_2$ source and of metering it to an outlet for a catheter for administration to the patient, having motorised means capable of actuating the intake of $CO_2$ into the metering device and of actuating the valves thereof in order to control the administration of the gas.

10 Claims, 7 Drawing Sheets

APPARATUS FOR ANGIOGRAPHY BY THE INJECTION OF CO$_2$

DESCRIPTION

The present invention is to provide an apparatus for angiography by the injection of CO$_2$, which has substantial advantages over the prior art.

As is known, angiography concerns methods of radiological diagnosis by the injection of a contrast medium in order to permit the assessment of vascular lesions, such as stenosis, occlusions, aneurysm, fistulas, etc. Generally, these procedures are carried out in vascular radiology rooms provided with the equipment necessary for carrying out the radiographic technique, normally with radiological systems which permit digital subtraction angiography, or DSA, under the best possible conditions.

Conventional contrast media are based on iodine which is radio-opaque to X-rays. However, iodated contrast media can cause allergies, are nephrotoxic and, likewise, can produce cardiovascular complications.

The introduction of the injection of high-purity or medical grade CO$_2$ under predetermined and known conditions, such as volume and pressure through a catheter, also enables angiographic processes to be carried out. The CO$_2$ displaces the blood in the vessel and briefly creates a gas bubble which moves in the direction of blood flow. While the gas is being injected, the digital subtraction angiography equipment takes a series of radiographic images in which the passage of the contrast medium through the vessel being studied is recorded. Afterwards, the best image recorded can be selected to be transferred to a physical support (radiography).

The angiography apparatus to which the present invention relates has advantageous functional features compared with currently known apparatus, providing means that permit the autonomous injection of CO$_2$ into the blood vessel, having a large number of regulating and control means which enable the process to be carried out and monitored with safety features which have been unknown hitherto and also providing practical means which, in a simple and readily transportable manner, make it possible to have available all the elements for carrying out angiography by injection of CO$_2$.

The apparatus to which the present invention relates basically comprises a foot carrying the CO$_2$ source, and a column carrying, at its upper portion, the movable arm, which is of an articulated type, forming two regions in the second of which the receiving support for the CO$_2$-metering device is installed. The movable arm unit is adjustable both in terms of rotation about an axis coinciding with the geometrical axis of the column and in terms of pivoting on the first member of the movable arm, which member is composed of an articulated parallelogram, and, likewise, on the second member of the movable arm, or the support for the metering device, which is also adjustable in terms of rotation with respect to the first arm member. The column accommodates a hand grip and a perfusion support of the type which can be adjusted in height. A screen which is rotatable about the geometrical axis of articulation of the two members forming the movable arm and which is also inclinable, enables the apparatus to be programmed and controlled.

This arrangement permits both an efficient and compact arrangement of all the members making up the apparatus, and efficient control of all the functions thereof.

Some drawings corresponding to a preferred embodiment of the apparatus of the present invention are appended by way of non-limiting example for a better understanding thereof.

Figure 1:
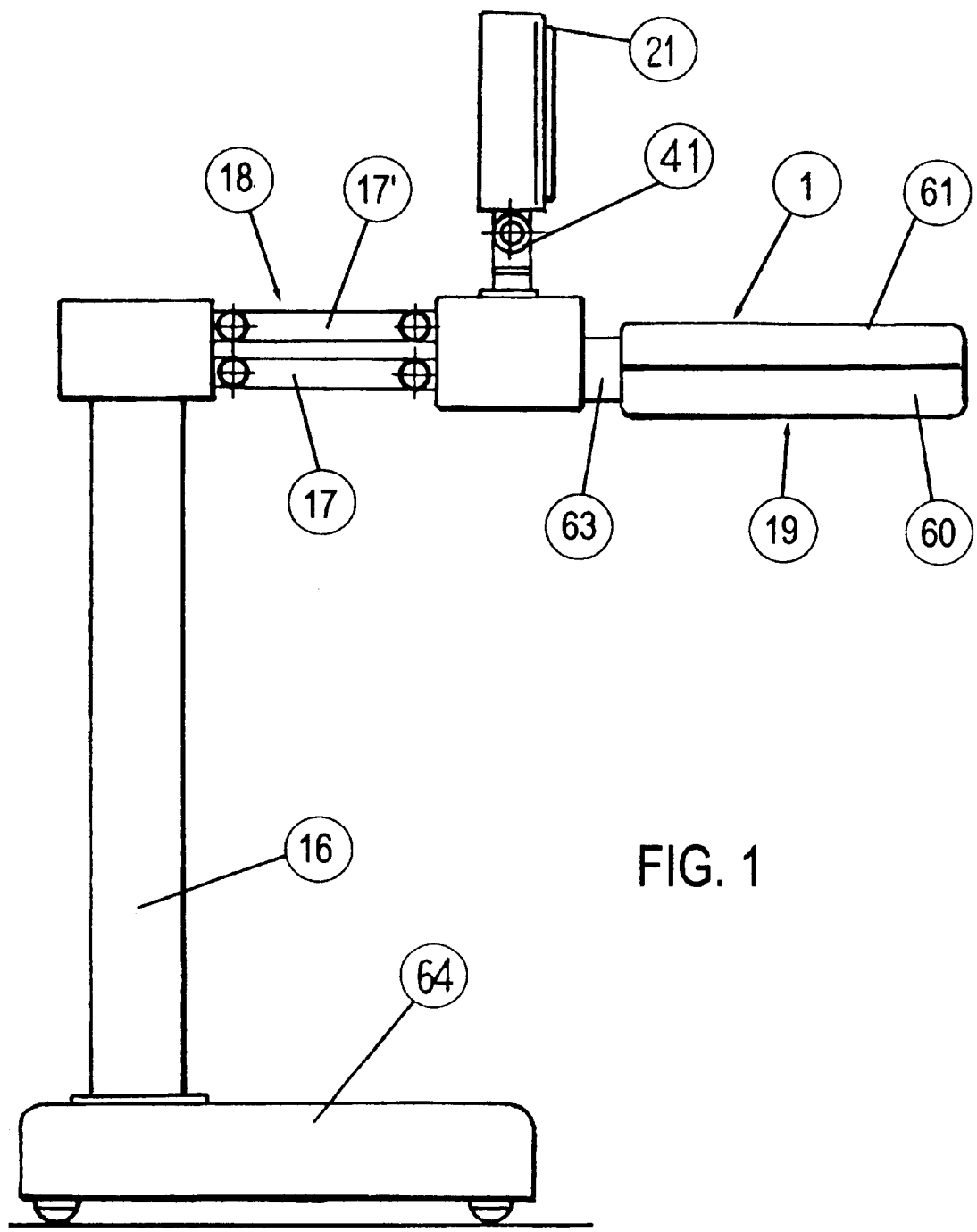
FIG. 1 is a side view of the apparatus.
Figure 2:
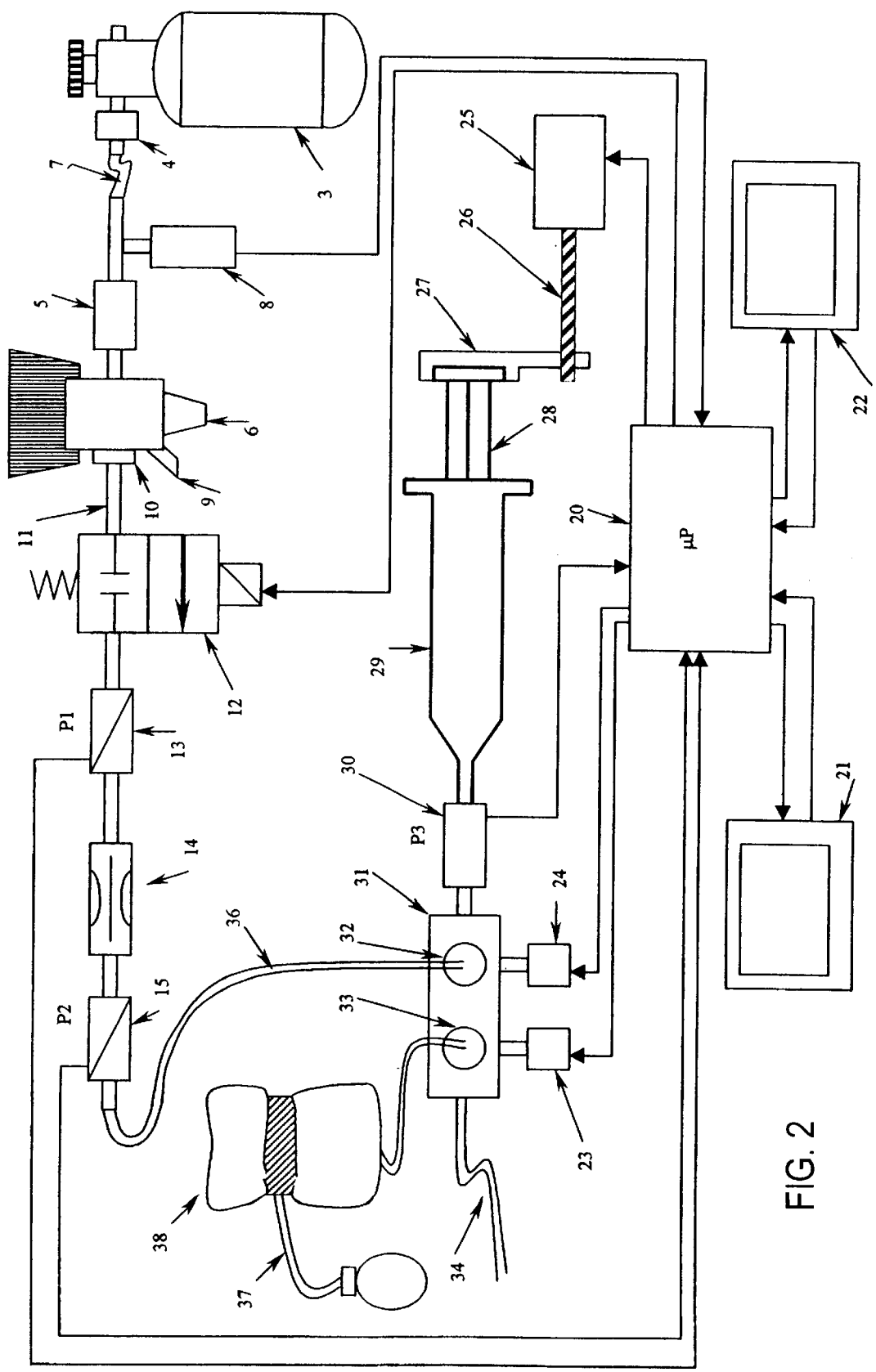
FIG. 2 shows schematically, in a block diagram, all of the members making up the apparatus.
Figure 3:
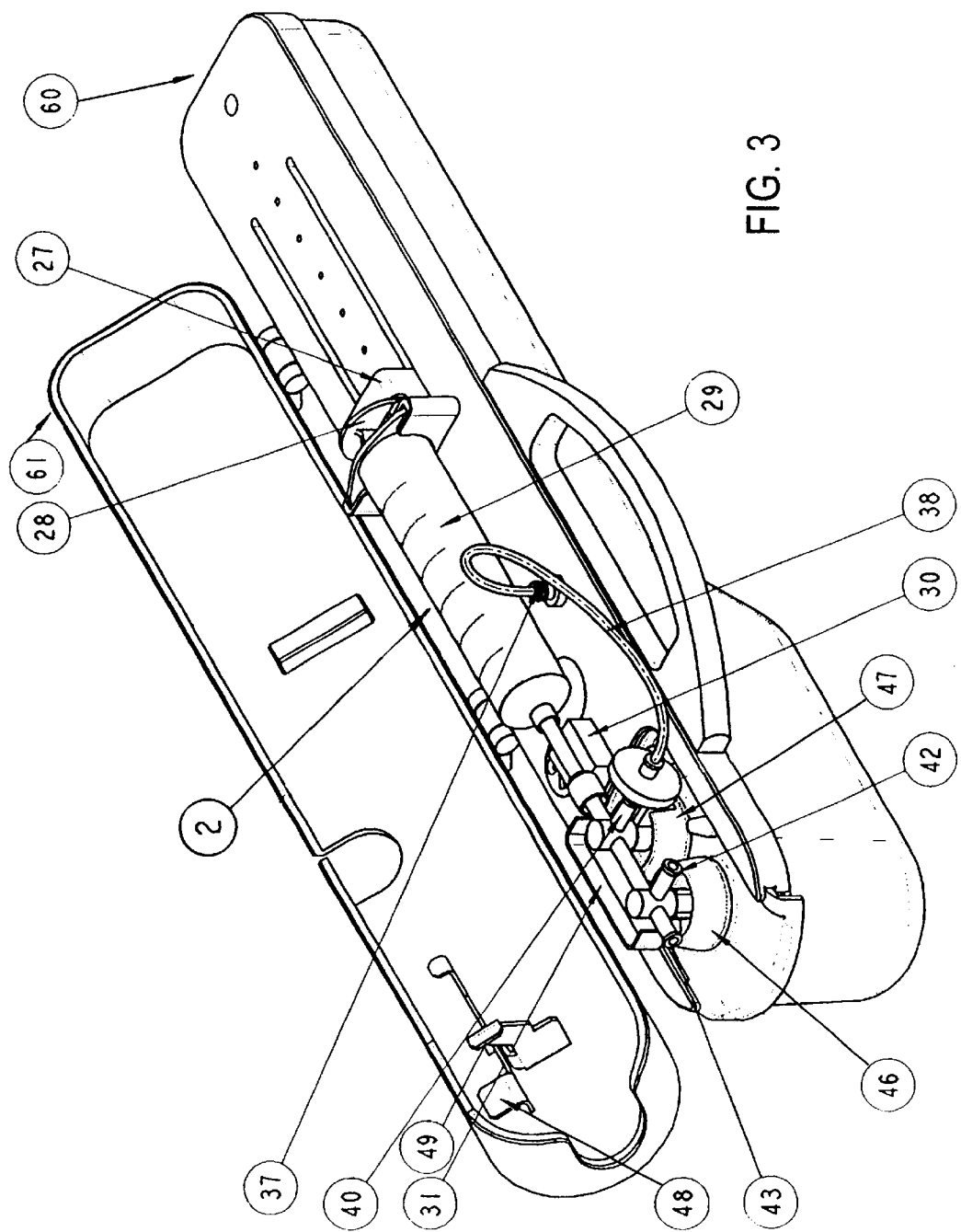
FIG. 3 is a perspective view of the second member of the movable arm in the open position.
Figure 4:
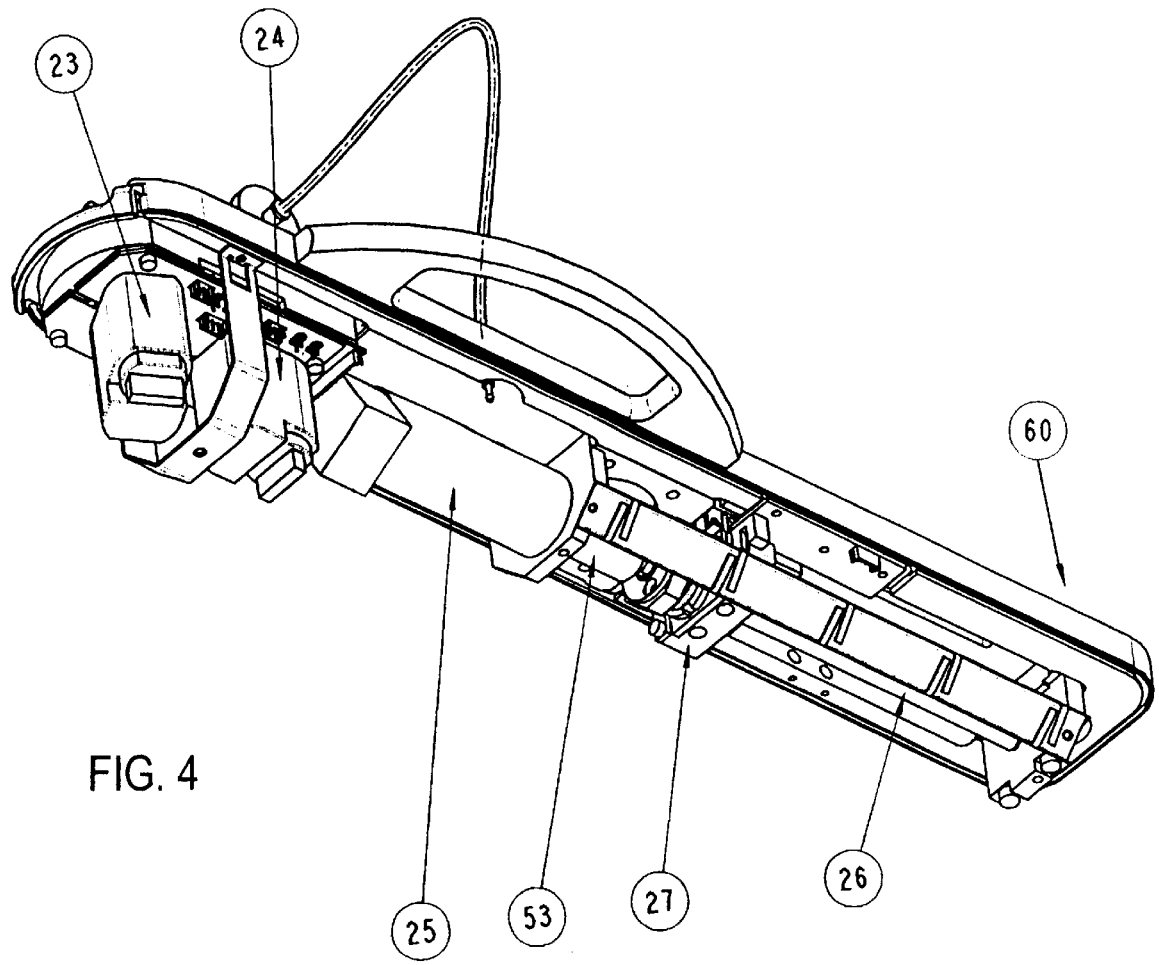
FIG. 4 is a perspective view of the base of the second member of the movable arm carrying the CO$_2$-metering device.
Figure 5:
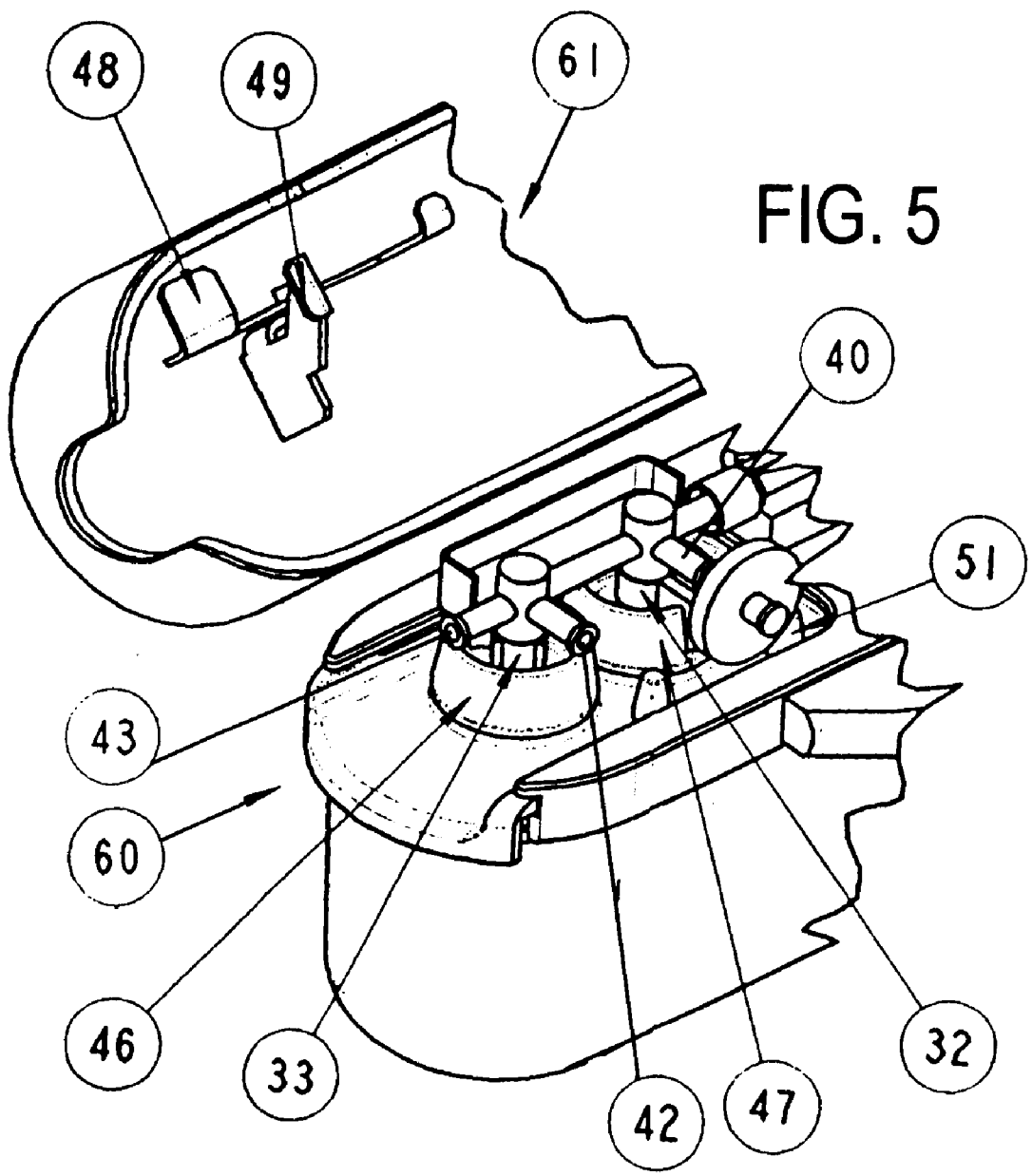
FIG. 5 is a perspective view of the end for operating the valves of the metering device.
Figure 6:
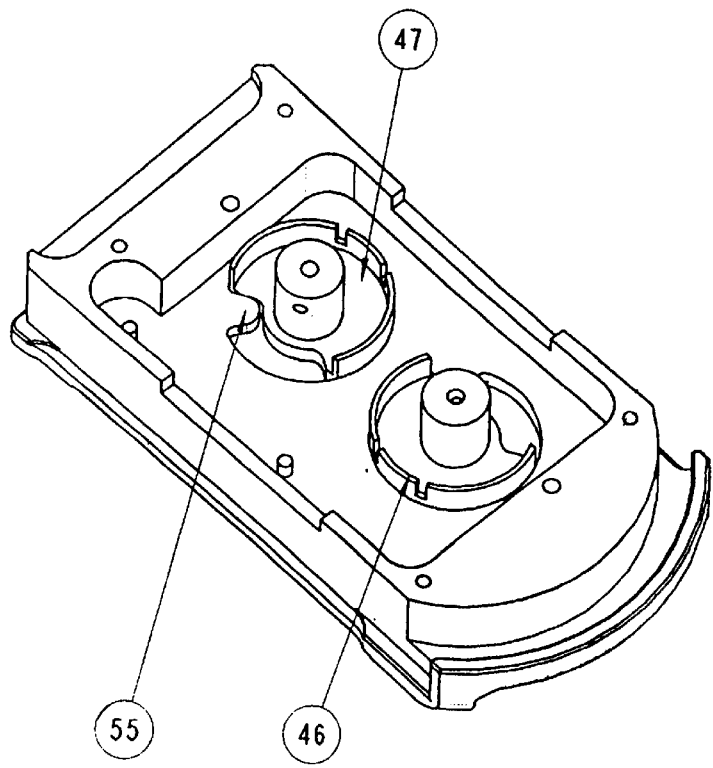
FIGS. 6 and 7 are details of the end of the arm represented in FIG. 5.
Figure 7:
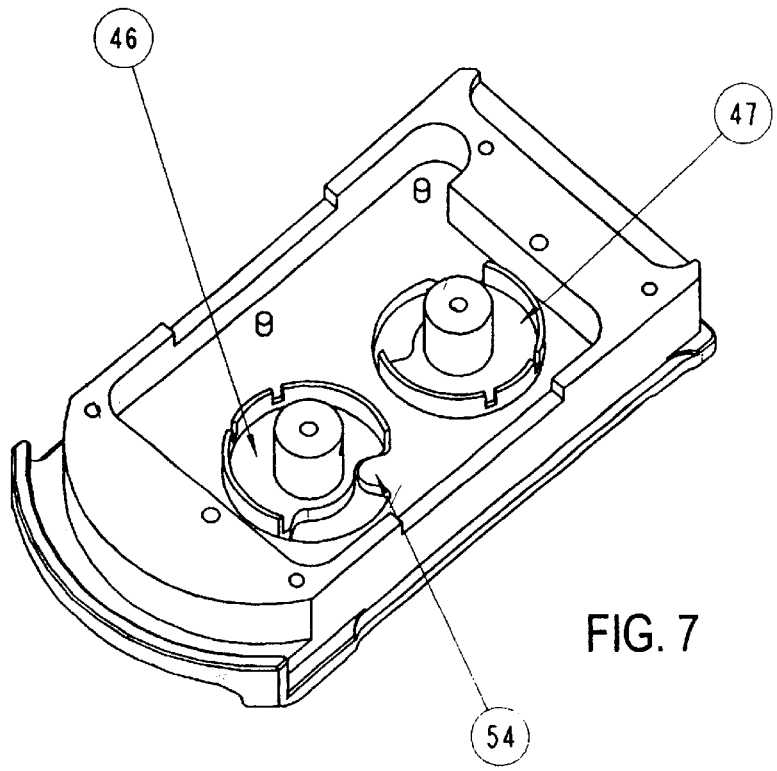
Figure 8:
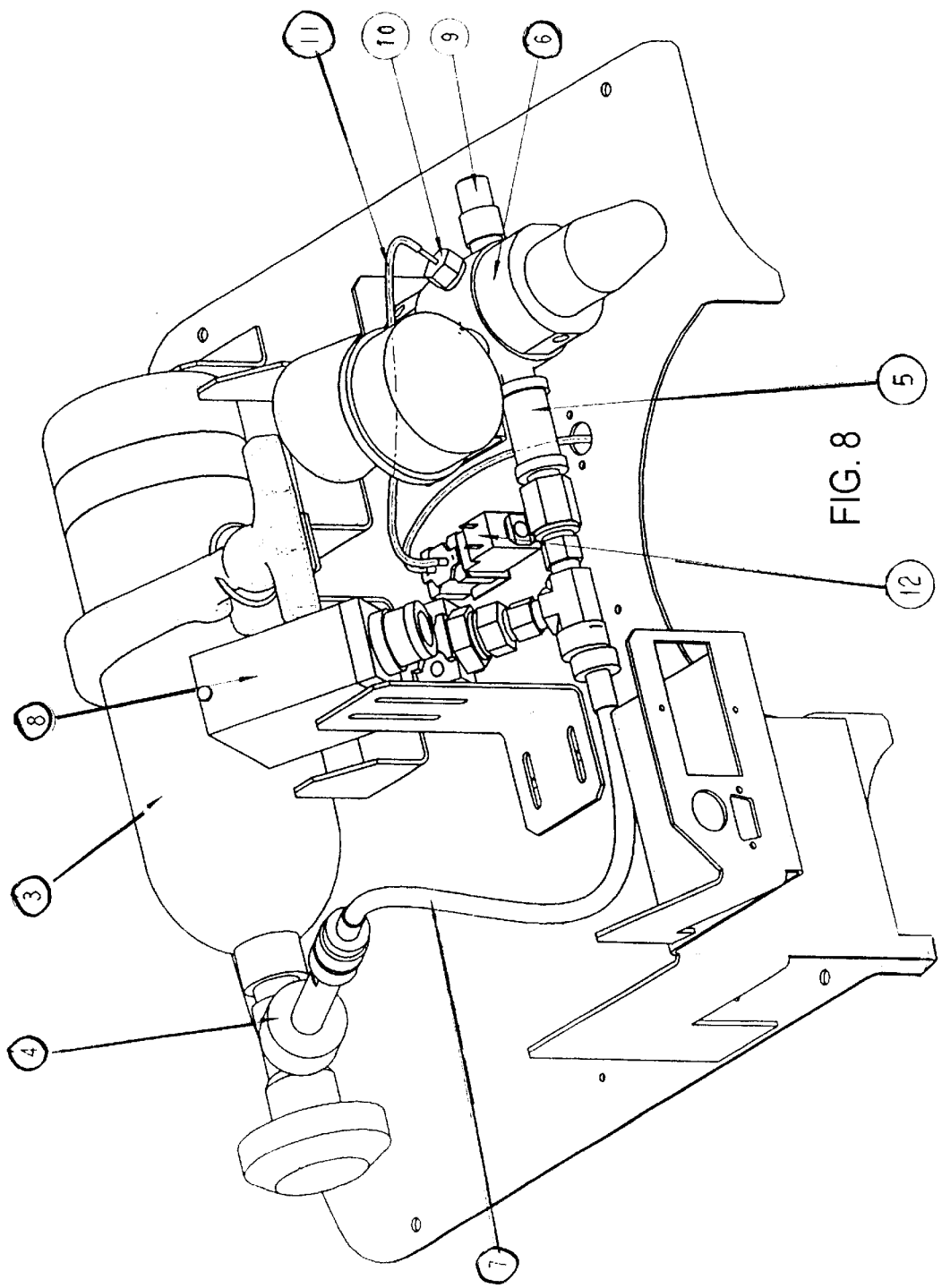
FIG. 8 is a perspective view of the unit made up of the CO$_2$ reservoir and the members for metering the CO$_2$.

As shown in the drawings, the apparatus which has been generally indicated 1 has a base 64, provided with wheels, which contains the carbon dioxide reservoir and from which extends the support column 16 carrying an upper, movable arm composed of the two members 18 and 19 which are articulated to one another by an intermediate shaft 63. The first member 18 of the movable arm is in the form of an articulated parallelogram having two arms 17 and 17' enabling it to pivot with respect to the upright position of the shaft 63 for the rotation of the member 19 of the arm. The member 19 has two component parts, a lower body or base 60 and a cover 61, which are to enclose the metering device and to interact therewith.

A screen 21 is arranged on the movable arm and has the ability to tilt and rotate about the articulation 41. At its starting point in the column 16, the movable arm 18 is also rotatable about an upright axis, and therefore there is a vary wide range of possible adjustment positions for the end of the arm 19 and for the screen 21. A perfusion support (not shown) is coupled to the upper portion of the column 16 and its position can be adjusted by vertical displacement.

The apparatus is in a form such that the gas supply passes from the base 64 to the metering unit accommodated inside the movable arm member 19, which is constituted by the base 60 and the cover 61, the unit being capable of being connected to a catheter for the introduction of carbon dioxide into the blood vessel being monitored in the patient. The screen 21 permits the programming and control of the angiographic process.

As will be appreciated, although the apparatus is basically described as a supplier of CO$_2$ for angiography, it could also work with any other appropriate gas, introducing it into the bloodstream of the patient in order to carry out the angiographic process.

The dose of gas, and also the supply pressure, are controlled by the apparatus after the programming has been fixed by the apparatus with the desired reference values.

The constitution of the apparatus provides for the catheter to be washed with a physiological solution while waiting for exploration to commence and also makes it possible to synchronise the supply of carbon dioxide with an X-ray apparatus.

Metering is effected by a single-use metering device 2.

As will be appreciated from the drawings, the carbon dioxide passes from the source 3 to the metering device 2 which supplies it to the patient in a controlled manner. The gas from the source 3 flows through the connection piece 4 and a flexible tube 7, is purified by the 0.5-$\mu$m filter 5 and its pressure is set by the two-stage pressure regulator 6. The pressure switch 8 informs the control card 20 when the pressure of the source 3 is less than 10 bar, in which case the user is warned of the advisability of refilling it. A safety valve 9 inserted in the pressure regulator 6 releases the gas to the atmosphere when it exceeds the reference pressure of said valve. The carbon dioxide passes through the connection 10 and the duct 11 to the electrovalve 12, the closing and opening of which are brought about by the control card 20 in accordance with the stage of the process the apparatus has reached.

At the moment of supplying gas to the metering device 2, the electrically operated valve 12 is opened by the control card 20, the carbon dioxide passing through a flow meter formed by the pressure sensor 13, the fixed-opening throttle 14 and the pressure sensor 15. The principle by which the meter operates is the difference in pressure produced between the ends of a throttle when gas passes through it, which difference in pressure is directly proportional to the flow of the gas. The duct 36, the luer-lock connection 37 and the duct 38 form the circuit through which the carbon dioxide flows from the outlet of the pressure sensor 15 to the 0.22 $\mu$m filter arranged in the inlet connection 40 of the metering device 2.

Before supplying the carbon dioxide to the patient, the metering device 2 has to be completely emptied of air because the introduction of air into the vascular system could cause a gas embolism. To that end, the apparatus I carries out several filling-emptying cycles on the metering device 2 so that any air in the circuits is released to the atmosphere. Once that operation has been completed, the metering device is ready to supply carbon dioxide to the patient.

In detail, the procedure for emptying the metering device 2 is as follows: the motor 24 is controlled by the control card 20 and causes the member 46 and, because it is inserted therein, the valve 32 of the manifold 31, to rotate until the connection 40 is in communication with the pressure sensor 30. At that moment, the control card 20 activates the motor 25 which, because it is connected to the screw 26 by means of the flexible coupling 53, brings about the rotation of said screw and, therefore, the displacement of the housing 27 and the plunger 28 of the syringe 29, which plunger is inserted in said housing. The movement stops when the plunger frees the volume of the syringe 29, for example 60 ml, and, while this situation continues, the carbon dioxide flows into it because it is at a positive pressure. The control card 20 maintains this situation for a predetermined period, allowing the gas time to fill all of the space which the plunger has freed, and, immediately afterwards, activates the motors 23 and 24 until the valves 33 and 32 are in a position such that the carbon dioxide is released to the atmosphere by way of the distal end 43 of the manifold 31, passing by way of the pressure sensor 30. At the same moment as this occurs, the control card 20 acts on the motor 25 to cause it to move the plunger 28 until the syringe has been completely emptied, at which moment this movement stops and the valves 33 and 32 of the manifold 31 return to their closed position. The entire cycle is repeated three times.

The user can select the supply of a physiological washing solution throughout the time during which intervention lasts, thus preventing the entry into the catheter of blood, which could form clots. The control card 20 acts on the motor 23 which, because it is fixed securely to the housing 46, displaces the valve 33 of the manifold 31, which valve 33 is inserted inside said housing, to its positions of perfusion, injection or closure, depending on the stage which the intervention has reached.

The procedure for supplying carbon dioxide can start once the metering device has been drained, and can be repeated as many times as desired, provided that a waiting period is observed between consecutive injections, which can be programmed to be from 60 to 300 seconds, and that the total volume of gas supplied to the same patient does not exceed a value which can be programmed to be from 500 to 5000 ml.

In detail, the supply process is started by the control card 20, once a check has been carried out to ensure that all of the safety conditions have been met. The first step of the sequence is to administer a small amount of carbon dioxide in order to empty the catheter of the physiological washing solution. To that end, the control card 20 causes the motor to bring about the rotation of the member 47 and, because it is inserted therein, the valve 32 of the manifold 31, until the connection 40 is in communication with the pressure sensor 30. At that moment, the control card 20 activates the motor 25 which, being connected by way of the flexible coupling 53 to the screw 26, brings about the rotation of the latter and, therefore, the displacement of the housing 27 and the plunger 28 of the syringe 29, which plunger 28 is inserted in said housing. While the movement lasts, the carbon dioxide flows into the syringe 29 because it is at a positive pressure, and it stops when the plunger frees the volume of the syringe 29 which corresponds to the programmed dose of gas for washing the catheter, converted to the volume at the pressure read by the sensor 30, by applying the law of ideal gases. The control card 20 maintains this situation for a predetermined period, allowing the gas time to fill all of the space which the plunger has freed and, immediately afterwards, it activates the motor 24 until the valve 32 is in the closed position. It then causes the motor 25 to bring about the displacement of the plunger 28 of the syringe 29 until the pressure reader 30 indicates that the pressure programmed for the dose for washing the catheter has been reached. At that moment, the control card 20 acts on the motors 23 and 24 to cause them to displace the valves 32 and 33 until they reach the open position, so that the carbon dioxide is released to the extension of the catheter 34 and, from there, to the patient's blood vessels. Throughout the period of supplying gas, the control card 20 reads the pressure sensor 30 continuously, and acts accordingly on the motor 25 in order to keep the pressure constant, so that the washing of the catheter and the introduction of carbon dioxide into the patient's blood vessels are carried out in a uniform and controlled manner, avoiding compression and pressure peaks. When the stroke of the plunger 28 is complete and all of the gas has been displaced, the control card 20 returns the valves 32 and 33 to their closed position by acting on the motors 23 and 24.

When the process of washing the catheter has been completed, the control card 20 observes an absorption time programmed by the user before starting any other movement. Thus, the carbon dioxide has time to dissolve in the patient's blood and to be eliminated by respiration without impairing the quality of the images. When the absorption time has elapsed, the control card 20 starts another gas supply cycle like that described in the previous paragraph, but with the dose and the pressure programmed by the user. In addition, it generates an acoustic signal at a programmed time before carrying out the administration of the carbon dioxide, so that the user can generate the masking images for the subsequent processing of the images obtained.

Otherwise, the cycle of introducing gas into the syringe, pressurising and supplying at a constant pressure is identical to the one already described.

For the whole period that intervention lasts, the apparatus 1 carries out exhaustive checks to ensure that the gas is being supplied correctly, and also to avoid any risk to the patient and user. The safety measures taken are the following:

Protection against loss of sealing or incorrect connection of the singleuse metering device 2. This could bring about the entry of air into the metering device and the subsequent supply thereof to the patient, with the risk of gas embolism which this would involve. In order to prevent this, whenever the syringe 29 is filled with carbon dioxide, a check is carried out by means of the flow meter formed by the unit composed of the pressure sensors 13 and 15 and the throttle 14 to ensure that the flow is cancelled a few seconds after the plunger 28 has been stopped. If it has not been cancelled, this will indicate a leak or incorrect connection in the metering device and therefore the process is stopped and an error message is generated on the screens 21 and 22.

Protection against excessive pressure in the carbon dioxide supplied. Although, owing to the configuration of the machine, this would not be dangerous to the patient, it would nevertheless indicate some obstruction or malfunction, and therefore, if a pressure higher than 2000 mmHg is measured in the sensor 30, the process which was being carried out is stopped and an error message is generated on the screens 21 and 22.

Protection against failure of the pressure sensor 30. Since the supply pressure is regulated as a function of the sensor reading, failure of the sensor would cause the gas to be administered under incorrect conditions. In order to detect any possible anomaly therein, its reading is compared with that of the internal sensors 13 and 15, an error message being generated if there is any discrepancy.

Protection against subsequent exploration without observing the period for the absorption of carbon dioxide. Despite being a gas which is very soluble in blood, excessively prolonged intervention could cause an excessive concentration of carbon dioxide in the blood, with the consequent risk to the patient. In order to prevent this, the control card 20 generates an internal clock and obliges interventions to be spaced by a safety period programmable to be from 60 to 300 seconds, preventing the start of an injection cycle until the safety period has elapsed.

Protection against the supply of an excessively high dose of carbon dioxide to the same patient. Protection is two-fold: on the one hand, the use of a single-use metering device 2 prevents 100 ml being exceeded in a single injection and, on the other hand, the control card 20 adds up the volume supplied in successive explorations carried out on the same patient, preventing it from exceeding a value programmed to be from 500 to 5000 ml.

Protection against direct connection of the carbon dioxide source to the patient's blood vessels. This could have such serious effects as ischaemia, hypotension, etc. To prevent this happening, the housings 46 and 47 of the valves 32 and 33 are designed in such a manner that they can never be in a position such that, if the electrically operated valve 12 is closed, they would permit the direct supply of gas from the source 3 to the patient's blood vessels. The tab 54 prevents the housing 46 from rotating beyond the positions of injection, perfusion with physiological solution, and closure. The tab 55 prevents the housing 47 from rotating beyond the positions of introducing carbon dioxide into the syringe 29, injection, and closure.

Protection against the selection of physiological washing solution without the source being connected to the connection 42 of the manifold 31. Owing to arterial pressure, this would cause blood to enter the catheter and the extension of the catheter, with possible formation of clots. To prevent this, a rocker 48 is introduced which pivots on the support 49, pressing a detector 51 if a luer-lock connection with a female thread is arranged in the connection 42. If this happens, the user is able to activate the option of washing with physiological solution. If not, an error message is generated if the user enables irrigation.

Protection against draining of the single-use metering device 2 with the patient connected. This would bring about the administration of air to the patient's blood vessels, which could result in a gas embolism. In order to prevent this, in addition to the intermittent warnings to the user and the obligation to keep the activation key pressed for one and a half seconds, before starting the movement of the plunger 28, the control card 20 acts on the motors 23 and 24 until the valves 32 and 33 are in their open position, enabling the sensor 30 to detect the existence of a pressure higher than atmospheric pressure if the patient is connected, which would bring about the immediate interruption of the draining process before starting to move the plunger 28 and, therefore, before supplying air to the patient.

What is claimed is:

1. A transportable apparatus for performing angiography by the injection of a gasous contrast medium, the apparatus comprising:

a support base having wheels and carrying a source for the supply of the gaseous contrast medium under regular pressure, a support foot at the top of the support base, an articulated arm provided at the top of the support foot, and having a programming and control screen and a receiver for receiving an exchangeable metering device, the exchangeable metering device receiving the gaseous contrast medium by way of ducts coming from the gaseous contrast medium source and metering the gaseous contrast medium to an outlet of a catheter for administration to a patient, and motorized means for actuating the intake of the gaseous contrast medium into the metering device and for actuating valves thereof in order to control the administration of the gaseous contrast medium.

2. The apparatus according to claim 1, wherein the articulated arm comprises first and second arm members articulated to one another, the first arm member being coupled to the support foot, having an articulated parallelogram structure, and being rotatable about the axis connecting it to the support foot, the second arm member being rotatable about the axis of articulation to the first arm and carrying a unit, comprised of a base and cover, for receiving, activating and controlling the exchangeable gaseous contrast medium metering device.

3. The apparatus according to claim 1, wherein the first arm member is rotatable about an upright axis, inclinable about a horizontal axis, and carries a screen for the operational programming and control of the apparatus.

4. The apparatus according to claim 1, further comprising a microprocessor which controls the valves for the passage of gas from the supply source to the metering device, and the activation of the metering device and the valves controlling the entry and discharge of gaseous contrast medium with respect to the metering device and towards the administration catheter, wherein the microprocessor connected to a programming panel and to signaling screens.

5. The apparatus according to claim 1, wherein the body of the second member of the articulated arm carries connections for activating the valves for the discharge and entry of the gaseous contrast medium out of and into the metering device, each of the valves having an individual motor controlled by the microprocessor.

6. The apparatus according to claim 5, wherein the activators of the valves for the entry and discharge of gas into and out of the metering device are combined with rotation-limiting stops in order to prevent, in a positive and automatic manner, a direct connection of the source of carbon dioxide to the patient's blood vessels.

7. The apparatus according to claim 6, wherein the rotation stops for the valve-activating devices are constituted by tabs which project into the housing of the valve activators and which limit the rotation thereof.

8. The apparatus according to claim 2, wherein the cover of the second member of the articulated arm has a safety device preventing selection of physiological washing solution without the source being connected to the connection of a manifold carrying the entry and discharge valves, in order to prevent the patient's blood from entering the catheter.

9. The apparatus according to claim 8, wherein the safety device is formed by a rocker which pivots on a bearing support secured to the cover of the second arm member and activates a detector of the base of the second arm member.

10. The apparatus according to claim 1, wherein the gaseous contrast medium is $CO_2$.

* * * * *

UNITED STATES PATENT AND TRADEMARK OFFICE
CERTIFICATE OF CORRECTION

PATENT NO.      : 6,503,226 B1                                       Page 1 of 1
DATED           : January 7, 2003
INVENTOR(S)     : Enrique M. Gisper-Sauch It is certified that error appears in the above-identified patent and that said Letters Patent is hereby corrected as shown below:

Column 6,
Line 38, delete "regular" and substitute with -- regulated -- therefor.

Signed and Sealed this

Twenty-third Day of September, 2003

JAMES E. ROGAN
*Director of the United States Patent and Trademark Office*